United States Patent [19]

Polito

[11] 4,158,703
[45] Jun. 19, 1979

[54] T₃ UPTAKE TEST EMPLOYING COVALENTLY BOUND BOVINE SERUM ALBUMIN

[75] Inventor: Alan J. Polito, Costa Mesa, Calif.

[73] Assignee: Beckman Instruments, Inc., Fullerton, Calif.

[21] Appl. No.: 877,043

[22] Filed: Feb. 13, 1978

Related U.S. Application Data

[63] Continuation-in-part of Ser. No. 682,808, May 3, 1976, Pat. No. 4,081,245.

[51] Int. Cl.² .................... G01N 33/16; A61K 43/00
[52] U.S. Cl. ................................ 424/1; 23/230 B; 23/230.6; 260/112 B; 424/12
[58] Field of Search ............... 424/1, 12; 23/230.6, 23/230 B; 260/112 B

[56] References Cited

U.S. PATENT DOCUMENTS

| 4,081,244 | 3/1978 | Polito et al. | 23/230 B |
|---|---|---|---|
| 4,081,245 | 3/1978 | Polito | 23/230 B |
| 4,081,246 | 3/1978 | Polito et al. | 23/230 B |

Primary Examiner—Benjamin R. Padgett
Assistant Examiner—Christine M. Nucker

Attorney, Agent, or Firm—R. J. Steinmeyer; Robert S. Frieman

[57] ABSTRACT

An improved T₃ uptake test procedure characterized in that the separating agent employed therein comprises bovine serum albumin covalently coupled to a derivatized polysaccharide matrix by a bifunctional coupling agent selected from a group consisting of wherein n is an integer from 1 to 6 and wherein e is an integer from 1 to 2.

A separating agent comprising bovine serum albumin covalently coupled to a derivatived polysaccharide matrix by a bifunctional coupling agent selected from a group consisting of wherein n is an integer from 1 to 6 and wherein e is an integer from 1 to 2.

22 Claims, 1 Drawing Figure

T3 UPTAKE TEST EMPLOYING COVALENTLY BOUND BOVINE SERUM ALBUMIN

CROSS-REFERENCE TO RELATED APPLICATIONS

This application is a continuation-in-part of copending application, Ser. No. 682,808, filed May 3, 1976, now U.S. Pat. No. 4,081,245.

BACKGROUND OF THE INVENTION

1. Field of the Invention

This invention pertains to $T_3$ uptake test procedures and to a novel separating agent for use therein.

2. Description of the Prior Art

As early as 1939 (1), Treverrow reported that hormonal iodine compounds such as thyroxine constitute the major portion of the total serum iodine. Furthermore, these iodinated organic compounds could be distinguished from serum inorganic iodide because they are bound to serum protein. Since iodine constitutes 65 percent by weight of the thyroxine molecule, serum protein-bound iodine (PBI) was employed as an index of serum thyroxine ($T_4$). This indirect measurement of serum thyroxine was believed to be a good indicator of the thyrometabolic status of an individual (2,3,4). The normal range of PBI values was found to be 4–8 ug/100 ml; values below 4 ug/100 ml were consistent with hypothyroidism whereas values above 8 ug/100 ml were indicative of thyrotoxicosis (hyperthyroidism).

A major pitfall of the PBI test is its inherent lack of specificity since high levels of inorganic iodide, radioopaque dyes and certain drugs give abnormally high values. In 1964, Murphy and Pattee (5) introduced their competitive protein binding analysis (CPB) for serum thyroxine which solved most of the nonspecificity problems associated with the PBI test. Due to the fact that CPB tests for serum thyroxine also required an extraction of the $T_4$ from the remainder of the serum components, recovery variability has led to problems both in accuracy and precision.

Recently, radioimmunoassay (RIA) has become the method of choice for measuring serum thyroxine (6). The RIA technique can be run directly on serum without extraction and therefore yields a simple and yet highly specific test. In general, results from RIA are from 5 to 25 percent higher than those from CPB tests.

Although the direct measurement of serum thyroxine is not influenced by exogenous iodine, the value obtained will be influenced by the level of the circulating thyroxine binding proteins. A number of states which are totally unrelated to thyroid disease may cause abnormal serum levels of thyroxine. Changes in the serum level of circulating thyroxine binding proteins may cause the serum thyroxine level to be high or low even in the presence of normal thyroid function. Although the primary protein involved is thyroxine binding globulin (TBG), both thyroxine binding prealbumin (TBPA) and albumin also bind $T_4$. Normally $T_4$ is distributed as follows: 65% on TBG, 25% on TBPA, and 10% on albumin (7). In general, changes in TBG concentrations correlate much better with anomalies in thyroid function tests, such as the PBI or total thyroxine than do changes in TBPA (8).

Estrogen is one of the most important factors influencing the level of TBG, its effect being most notable in individuals receiving oral contraceptives or during pregnancy. In both cases TBG concentrations are markedly elevated and consequently due to the increased binding sites, the serum $T_4$ or PBI are elevated above normal.

High serum thyroxine values are also found in euthyroid subjects who have increased levels of TBG (idiopathic increase of TBG) or have hyperprotenemia. Androgens have an opposite effect to estrogens in that they lower the TBG concentration and lead to falsely low serum $T_4$ or PBI values. Other situations where the TBG concentration is below normal include an idiopathic decrease of TBG, the nephrotic syndrome and other hypoproteinimic states. Finally, a number of drugs such as diphenylhydantoin and salicylates, compete with thyroxine for binding sites on TBG, displace $T_4$ from the TBG and thus result in falsely low serum values.

Although the most accurate method to measure TBG concentrations involves the electrophoretic method of Orsorio et al. (9), the technique is too cumbersome for routine use. The method of choice which has been used for this purpose is one of the many variations of the triiodothyronine ($T_3$) uptake test. Hamolsky et al. (10) first performed this type of test and used red cells as the inert binder of $T_3$. All $T_3$ uptake tests are designed to assess the unsaturated binding capacity of serum proteins most notably TBG. The test is based on the fact that TBG binds $T_3$ less firmly than $T_4$ and therefore should not upset the equilibrium set-up between $T_4$ and TBG and, further, $T_3$ is not normally bound to TBPA.

In the $T_3$ uptake test an equilibrium is developed between the patient's serum, added labeled $T_3$ and an inert exogenous binder (separating agent) of the labeled $T_3$. One must add a sufficient amount of labeled $T_3$, e.g., $^{125}$I-labeled $T_3$, to saturate the binding sites on the TBG after which the labeled $T_3$ that is unbound is adsorbed by the separating agent and counted. Therefore, when the endogenous thyroxine level is increased, as in hyperthyroidism, serum TBG is relatively saturated and the $T_3$ uptake will be high. Conversely in the hypothyroid state where thyroxine output is low, the labeled exogenous $T_3$ will bind to the relatively unsaturated TBG yielding a low $T_3$ uptake.

The major variations in $T_3$ uptake methodology today are centered around the chemical nature of the separating agent. Ion exchange resins (11, 12, 13) hemoglobin saturated charcoal (14), Sephadex G-25 (15), inorganic crystalline materials such as magnesium silicate and aluminum silicate (16), and triiodothyronine antibody immobilized on the walls of polypropylene test tubes (17), all have been used as inert binders of labeled $T_3$. Careful timing and controlled temperatures are necessary in the conventional $T_3$ uptake tests using ion exchange resins, coated charcoal, or immobilized triiodothyronine antibody as the separating agent. However, when the inorganic crystalline material of Eisentraut (17) was incorporated into this diagnostic test, the sorption of the free labeled $T_3$ to this binder was neither critically time nor temperature dependent and this method gave highly efficient, fast and reproducible results.

Another $T_3$ uptake assay employs an insolubilized colloidal suspension of bovine serum albumin as the separating agent to resolve the protein bound $^{125}$I $T_3$ from the free $^{125}$I $T_3$ (18).

BIBLIOGRAPHY

1. Trevorrow, V., *J. Biol. Chem.*, 127:737 (1939).
2. De Mowbray, R. R., et al., *Lancet*, 2:511 (1952).

3. Sunderman, F. W., et al., *Amer. J. Clin. Path.*, 24:885 (1954).
4. Dailey, M. E., et al., *New Engl. J. Med.*, 254 (19): 907 (1956).
5. Murphy, B. E. P., et al., *J. Clin. Endocrinol.*, 24:187 (1964).
6. Chopra, I. J., *J. Clin. Endocrinol.*, 34:938 (1972).
7. Robbins, J., et al: Hormones in Blood, Gray, C. H., et al., eds., Academic Press, London, 2nd Ed., 1: 430 and 447 (1967).
8. Thomas, J. A. et al: Hormone Assays and Their Clinical Application, Loraine, J. A., et al., eds, Churchill Livingston, New York, 4th Ed., Vh. 12 (1976).
9. Osorio, C., et al., *Clin. Sci.*, 21: 355 (1961).
10. Hamolsky, et al., *J. Clin. Endocrinol.*, 17: 33 (1957).
11. Mitchell, M. L., et al., *J. Clin. Endocrinal. Metabi*, 20: 1474 (1960).
12. U.S. Pat. No. 3,414,383.
13. U.S. Pat. No. 3,206,602.
14. Herbert, J., et al., *J. Lab. & Clin. Med.*, 66 (5): 814 (1965).
15. Free, A. H., et al, *Clin. Chem.*, 15: 762 (1969).
16. U.S. Pat. No. 3,666,854.
17. Coleman, L. H., et al, *Clin. Chem.*, 23 (6): 938 (1977).
18. MAAT—3$^{tm}$, $^{125}$I T$_3$ Uptake Assly. for Determination of Unsaturated TBG Binding Capacities of Serum, Curtis Laboratories, Inc. 1948 E. 46$^R$ St, Los Angeles, California 90058 (June 24, 1976).

The above publications are incorporated herein in toto by reference.

SUMMARY OF THE INVENTION

This invention encompasses a T$_3$ uptake test procedure of the type wherein a solution is contacted with labeled T$_3$ and a separating agent. The serum bound labeled T$_3$ and the separating agent bound labeled T$_3$ are separated into two fractions and at least one of said fractions is measured. The T$_3$ uptake procedure of the instant invention is characterized in that the solution is contacted with a separating agent comprising bovine serum albumin covalently coupled to a derivatized polysaccharide matrix by a bifunctional coupling agent selected from a group consisting of

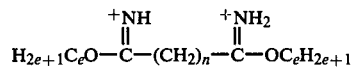

wherein n is an integer from 1 to 6 and wherein e is an integer from 1 to 2.

Also within the scope of the instant invention is a separating agent comprising bovine serum albumin convalently coupled to a derivatized polysaccharide matrix by a bifunctional coupling agent selected from a group consisting of

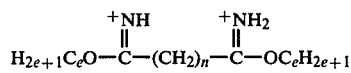

wherein n is an integer from 1 to 6 and wherein e is an integer from 1 to 2.

DESCRIPTION OF THE PREFERRED EMBODIMENTS

Figure 1:
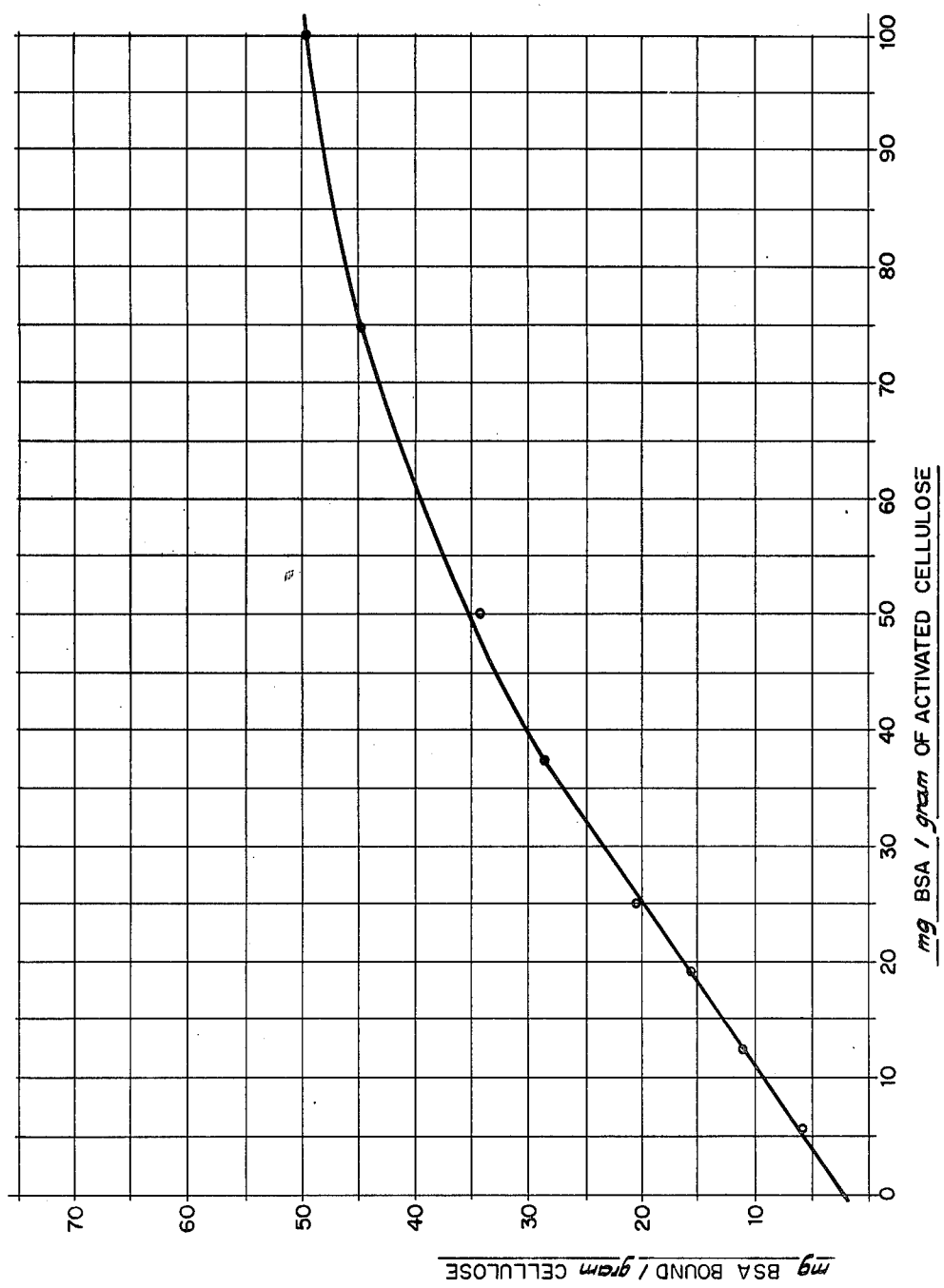
FIG. 1 is a graph depicting the extent of a reaction between various concentrations of bovine serum albumin and a unit amount of derivatized cellulose.

The novel separating agent within the scope of this invention comprises a derivatized polysaccharide matrix covalently coupled to bovine serum albumin by a bifunctional coupling agent selected from a group consisting of

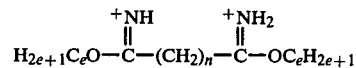

wherein n is an integer from 1 to 6 and wherein e is an integer from 1 to 2.

The polysaccharide matrix can be any matrix having a plurality of hydroxyl groups attached thereto as well as derivatives thereof. Preferred polysaccharide matrices include cellulosic polymers, dextran polymers, agarose, and derivatives thereof. Cellulosic polymers and derivatives thereof are the polysaccharide matrices of choice.

In one embodiment of this invention, the polysaccharide matrix is finely divided and has an average maximum dimension of 1 to 18 microns, preferably 10 to 15 microns. In this embodiment, the polysaccharide matrix can be spherical, linear, or have any other geometric configuration, provided that its average wet maximum dimension (diameter, width, length) is as described above. Several types of polysaccharide matrices are commercially available in this finely divided form. For example, Sephedex brand bead-formed dextran gel is available in several grades having a dry particle diameter of 10 to 40 microns as well as less than 10 microns. It is also possible to reduce the polysaccharide matrices' average wet maximum dimension by chemical techniques, for example, by hydrolysis. In order to hydrolyze said matrix, the polysaccharide matrix is, for example, contacted with an acidic solution, e.g., a 3 to 10 N solution of hydrochloric, sulfuric, or other suitable acid for a sufficient period of time, e.g., 2 to 4 hours. The acidic mixture is then neutralized with a basic solution, e.g., a 3 to 10 N solution of sodium or potassium hydroxide, etc., and subsequently washed and dried via standard techniques.

The polysaccharide matrices can be activated by any suitable method known to those skilled in the art. Exemplary reagents suitable for activating the polysaccharide matrix include cyanogen halide, epihalohydrin, haloacetyl halides, and divinyl sulfone. See Patty, *Industrial Hygiene and Toxocology*, Vol. 2, p. 634, Interscience, New York, N.Y. (1949), Axen, et al., *Nature* (Lond.), 214:1302 (1967), Rosner et al., *Biochem.*, 14:4813 (1975), Jagendorph et al., *Biochimica and Biophysica Acta*, 78:516 (1963), and Porath et al., *Nature New Biol.*, 238:261 (1972), said publications being incorporated herein in toto by reference. Preferably, a cyanogen halide or an epihalohydrin reagent is used to activate the polysaccharide matrix. More preferably, the polysaccharide matrix is activated by an epihalohydrin reagent or mixture thereof and most preferably, the polysaccharide matrix is activated by epichlorohydrin.

An alpha, omega-diaminospacer is then coupled to the activated polysaccharide matrix via one of the alpha, omega-diamospacer's amino groups thereby forming a derivatized polysaccharide matrix. To illustrate this point, if the polysaccharide matrix has been activated by a cyanogen halide reagent, the derivatized polysaccharide matrix will have the formula

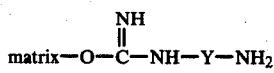

wherein the matrix is a polysaccharide matrix as defined above and wherein Y is a spacer. Exemplary spacers include $-(CH_2)_m-$, $-(CH_2)_b-NH-(CH_2)_c-$, $-\phi-(CH_2)_d-\phi-$, and $-\phi-N=N-\phi-$, wherein m is an integer from 1 to 12, preferably from 4 to 6, wherein b and c independently are integers from 1 to 6, preferably 2 to 3, and wherein d is an integer from 1 to 10, preferably 2 to 4. Preferably Y is $-(CH_2)_m-$.

As a further illustration of a derivatized polysaccharide matrix, if the polysaccharide matrix has been activated by an epihalohydrin reagent, the derivatized polysaccharide matrix will have the formula

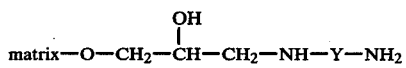

wherein matrix and Y are as assigned above.

Bovine serum albumin is covalently coupled to the derivatized polysaccharide matrix by the use of imidoesters. The imidoester has the general formula

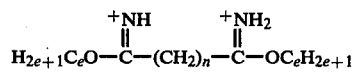

wherein n is an integer from 1 to 6, preferably from 4 to 6, and wherein e is an integer from 1 to 2. The use of these imidoesters enables one to covalently attach bovine serum albumin to solid supports through known chemical reactions which immobilize the bovine serum albumin through its lysine residues. Further, the presence of a positively charged matrix does not cause adverse nonspecific adsorption onto this invention's novel separating agents.

The novel separating agents within the scope of this invention can be prepared according to the following general procedure. An activating agent is contacted with the desired polysaccharide matrix in a solution having a desired pH. The pH can be in a general range from about 7.5 to about 10.0 with the particular pH being dictated by the activating agent and the polysaccharide matrix being used. The reaction can be allowed to proceed at room temperature. The activating reagent is allowed to remain in contact with the polysaccharide matrix for a sufficient period of time, from about 5 minutes to about 5 hours, to enable the matrix to become activated. The excess activating reagent is removed from the activated polysaccharide matrix by washing said matrix with a suitable medium, e.g., water, buffer (e.g., sodium bicarbonate), etc. The activated matrix is then suspended in a suitable medium, e.g., an aqueous solution of dimethylformamide. The desired alpha, omega-diaminospacer is then added to the suspended activated polysaccharide matrix and the reaction is allowed to proceed for about 1 to 10 hours at room temperature. The excess alpha, omega-diaminospacer is removed from the derivatized polysaccharide matrix by washing said matrix with a suitable medium, e.g., a solution of dimethylformamide, followed by a washing with a suitable buffer, e.g., a sodium bicarbonate buffer. After this double washing procedure, the derivatized polysaccharide matrix is suspended in suitable buffer, e.g., a sodium bicarbonate buffer.

The bifunctional coupling agent or mixture thereof is dissolved in a basic solution at about 4° C. If necessary, the pH is adjusted to about 8 to 9. The suspended derivatized polysaccharide matrix is then contacted with a dissolved bifunctional coupling agent and the mixture is rotated at about 4° C. for about 1 to about 5 hours.

After removing the excess bifunctional coupling agent via any standard technique, the coupled derivatized polysaccharide matrix is suspended in a mixture containing a suitable buffer, e.g., a sodium bicarbonate buffer, and bovine serum albumin. The mixture is rotated for about 10 to about 24 hours in a cold environment. The separating agent is then thoroughly washed with a suitable buffer, e.g., a sodium bicarbonate buffer, and then suspended in a suitable buffer having a pH of about 8, e.g., a barbital buffer containing about 0.1% gelatin.

The novel separating agent within the scope of this invention and as prepared by the above general procedure has the schematic structure

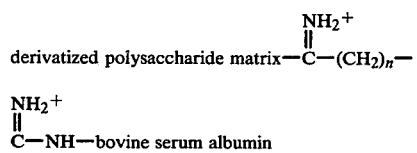

wherein derivatized polysaccharide matrix and n are as defined above. The preferred separating agent within the scope of this invention has the formula

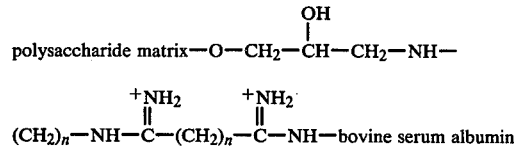

wherein polysaccharide matrix, m, and n are as defined as above.

The $T_3$ uptake test procedure of the instant invention entails contacting solutions with labeled $T_3$ and the novel separating agent of the instant invention; separating serum bound labeled $T_3$ and separating agent bound labelled $T_3$ into two fractions; and measuring at least one of said fractions via techniques well known to those skilled in the art. See Sunderman, F. W. et al., *Laboratory Diagnosis of Endocrine Diseases*, Ch. 19, Warren H. Green, Inc. St. Louis, Mo. (1971), said publication being incorporated herein in toto by reference.

In one preferred embodiment, the $T_3$ uptake procedure entails a method in which continuous agitation and thereby the need to stopper the tube is eliminated. See Chan et al., *Ann. Clin. Biochem.*, 12:173 (1973), said publication being incorporated herein in toto by reference. Preferably, the $T_3$ uptake procedure of the instant invention is a radio-assay procedure which technique is well known to those skilled in the art. See Skelley et al., *Clinical Chemistry*, 19(2):146 (1973), said publication being incorporated herein in toto by reference. Any suitable radioactive label, e.g., $^{131}I$ and $^{125}I$, can be employed. The preferred label is $^{125}I$.

The following examples are provided for the purpose of further illustration only and are not intended to limitations on the disclosed invention.

EXAMPLE 1

Microcrystalline cellulose (9 grams) Type 50 (50 micron average particle size) were added to 30 ml of a 6 N hydrochloric acid solution and the mixture was stirred for a period of about 18 hours at room temperature. After a 4 hour reaction time, the mixture was neutralized with a 6 N solution of sodium hydroxide and the hydrolized cellulose was washed with 1200 ml of water. The packed cellulose was further washed with 300 ml of methanol followed by 100 ml of diethyl either. The gel residue was suspended with 100 ml of either and dried under reduced pressure.

Epichlorohydrin (3 ml) was added to a mixture of 6 grams of hydrolyzed microcrystalline cellulose Type 50 in 30 ml of 1 N sodium hydroxide with vigorous stirring at room temperature. After 2 hours, the excess epichlorohydrin was removed by washing with 1 liter of water. The washed, activated cellulose matrix was then suspended in 60 ml of a 50% aqueous solution of dimethylformamide. To this suspended activated matrix was added 0.85 grams of 1,6-hexadiamine. The reaction was allowed to proceed with stirring for 2 hours at room temperature and then the excess 1,6-hexadiamine was removed by washing with 1 liter of a 50% aqueous solution of dimethylformamide. After washing with 1 liter of 0.1 M sodium bicarbonate, the derivatized cellulosic marix was suspended in 0.1 M sodium bicarbonate to give a 1.1 mixture of derivatized matrix to sodium bicarbonate.

Dimethyl adipidate (0.735 grams, 3 millimoles) was dissolved in 0.6 ml of cold 5 N sodium hydroxide solution with stirring at 4° C. After the addition of 0.6 ml of cold 0.1 M sodium bicarbonate, the pH was adjusted to 8.5 with 1 N sodium hydroxide. To this solution was added 6 ml of 0.1 M sodium bicarbonate containing 0.8-1.0 grams of derivatized cellulose (1:1 solution from above) and the mixture was rotated at 4° C. for about 2 hours. The total reaction volume was made 10 ml by the addition of cold 0.1 M sodium bicarbonate.

After the removal of the excess dimethyl adipidate, the support was suspended in 9 ml of 0.1 M sodium bicarbonate (4° C.) and 2.0 ml of cold 0.1 M sodium bicarbonate containing from 25-150 mg of bovine serum albumin (BSA) were added. After the mixture was rotated for 2 hours at 4° C., the immobilized protein was thoroughly washed with 0.1 M sodium bicarbonate and finally suspended in 20 ml of barbital buffer, pH 8.0, containing 0.1% gelatin and 0.01% Triton X-100 brand surfactant.

The extent of the reaction between various concentrations of BSA and 1 gram of the derivatized cellulose was monitored using $^{125}$I-labeled BSA. As FIG. 1 indicates, the activated cellulose has the potential to covalently bind to about 50 milligrams of BSA per gram of gel. To obtain this level of saturation one must use 100 mg of BSA in the procedure given above.

EXAMPLE 2

In order to test the effectiveness of the separating agent as a function of BSA bound per gram of gel, the following protocol was employed in a $T_3$ uptake test:

20λ—Sample

500λ—$^{125}$I-labeled $T_3$ is barbital buffer, pH 8.0, containing 0.1% gelatin 500λ—Separating agent in barbital buffer, pH 8.0, containing 0.1% gelatin and 0.01% Triton X-100 brand surfactant (prepared in Example 1)

The reagents were added in the order given, immediately vortexed and centrifuged at 1000×g for 10 minutes. (All manipulations were performed at room temperature.) After the supernatants were decanted, the gels were analyzed for radioactivity. Table I gives the B/T values obtained for different controls, using as secondary binders, gels prepared by reacting various quantities of BSA with 1 gram of activated cellulose.

Table I

| B/T Values Obtained from Gels Prepared by Reacting Different Quantities of BSA with 1 gram of Activated Cellulose | | | | |
|---|---|---|---|---|
| 1 gram/20 ml | 25 mg BSA | 50 mg BSA | 100 mg BSA | 150 mg BSA |
| Beckman Reference Serum | 29.78 | 29.90 | 29.45 | 28.78 |
| Beckman Control Serum | 25.78 | 26.26 | 25.72 | 25.39 |
| Hyland A | 23.67 | 22.56 | 22.28 | 22.66 |
| Hyland B | 30.63 | 28.29 | 30.00 | 27.18 |
| Hyland C | 34.07 | 35.48 | 33.56 | 33.74 |
| NML Reference Serum | 28.56 | 28.20 | 27.88 | 27.37 |
| Maximum Binding | 62.07 | 64.44 | 63.70 | 63.76 |
| 1 gram/40 ml | 25 mg BSA | 50 mg BSA | 100 mg BSA | 150 mg BSA |
| Beckman Reference Serum | 19.55 | 18.20 | 18.34 | 17.67 |
| Beckman Control Serum | 16.12 | 15.99 | 15.73 | 15.64 |
| Hyland A | 15.50 | 13.73 | 13.45 | 13.86 |
| Hyland B | 19.62 | 17.00 | 18.80 | 16.40 |
| Hyland C | 22.44 | 22.69 | 21.11 | 21.25 |
| NML Reference Serum | 17.18 | 17.93 | 17.36 | 16.72 |
| Maximum Binding | 45.52 | 48.29 | 47.36 | 46.81 |
| 1 gram/80 ml | 25 mg BSA | 50 mg BSA | 100 mg BSA | 150 mg BSA |
| Beckman Reference Serum | 11.37 | 11.34 | 11.79 | 11.42 |
| Beckman Control Serum | 10.17 | 10.58 | 9.88 | 9.71 |
| Hyland A | 9.74 | 8.65 | 9.39 | 8.16 |

Table I-continued
B/T Values Obtained from Gels Prepared by Reacting Different Quantities of BSA with 1 gram of Activated Cellulose

| | | | | |
|---|---|---|---|---|
| Hyland B | 12.12 | 10.78 | 11.73 | 10.16 |
| Hyland C | 14.38 | 13.71 | 13.19 | 12.95 |
| NML Reference Serum | 10.85 | 10.80 | 11.15 | 10.14 |
| Maximum Binding | 31.24 | 33.63 | 31.96 | 32.10 |

It is readily apparent from Table I that the B/T values for the controls remain constant regardless of the binder used. As FIG. 1 indicates, when 25 mg of BSA are reacted with 1 gram of activated cellulose, approximately 20 mg are bound; whereas in the case of 100 mg of BSA per gram of activated gel, 50 mg of BSA are attached. Thus even though more protein is actually bound to the cellulose as one goes from 25 to 100 mg of BSA, the effective binding ability of these two gels remains constant. This phenomenon may be explained by the theory that only a given amount of BSA or any of these gels is readily accessible to bind the label $T_3$. Although the binders may contain more BSA as one goes across Table I, most of the protein cannot participate in the reaction due to steric constraints.

Furthermore, as shown on Table I, the B/T values stay relatively constant as one dilutes the various gels. This data suggests that the $T_3$ uptake values one would obtain should be independent of the separating agent concentration over the range covered. An optimal solution of 1 gram of separating agent per 40 ml of buffer was chosen for use in the remaining examples since at this concentration the gel is readily pipetted and also gives a B/T value for the Beckman reference serum (BRS) of approximately 18-20%. This represents approximately 30,000 c.p.m. and thus should reduce both counting error and counting time.

Finally, since the effective binding capacity of 1 gram of cellulose obtained by reaction with 25 mg of BSA or 150 mg of BSA were equal, it was decided to use 25 mg of BSA per gram of cellulose in the remaining example.

EXAMPLE 3

Table II shows the effect of incubation time on the B/T values for different controls. It is readily apparent that the binding of the $T_3$ label is independent of time up to at least 40 minutes.

Table II
Time Independence on B/T Values

| Controls | 0 Min. | 10 Min. | 20 Min. | 40 Min. |
|---|---|---|---|---|
| Beckman Reference Serum | 19.56 | 20.31 | 20.98 | 20.21 |
| Beckman Control Serum | 16.37 | 16.16 | 16.08 | 16.66 |
| Hyland A | 15.36 | 15.35 | 14.42 | 14.10 |
| Hyland B | 18.01 | 18.18 | 17.78 | 17.71 |
| Hyland C | 25.97 | 25.94 | 26.20 | 26.47 |

EXAMPLE 4

The ratios of sample B/T to Beckman reference serum B/T as a function of temperature are given in Table III. When the results obtained at room temperature are correlated to those obtained at 4° C. and 37° C., one finds a linear correlation of 0.988 and 0.990, respectively. The slope and the intercept, on the other hand, appear to be different. However, since in both instances one is dealing with a small number of data points obtained from a planned pairing of samples (not independently and randomly chosen values), a pair t test may be employed to estimate the bias. See Mendenhall, W., *Introduction to Probability and Statistics,* Duxbury Press, North Scluate, Massachusetts, 4th ed., p. 228 (1975), said publication being incorporated herein in toto by reference. One may calculate the slope from the following equation, because the intercept or bias in both cases are indistinguishable from zero (see Bennett et al., *Statistical Analyses in Chemistry and the Chemical Industry,* John Wiley & Sons, Inc., New York, N.Y., p. 232 (1953), said publication being incorporated herein in toto by reference):

$$m' = \frac{\sum_{i=1}^{n}(x_i y_i)}{\sum_{i=1}^{n}(x_i^2)}$$

The results prove that the ratio values are not critically dependent upon incubation temperature. A similar treatment of the data presented in Table IV shows that the same ratio values are also not critically dependent on sample size.

Table III
Sample (B/T)/Beckman Reference Serum (B/T) as a Function of Temperature

| Controls | Room Temp. | 4° C. | 37° C. |
|---|---|---|---|
| Beckman Control Serum | .884 | .895 | .916 |
| Hyland A | .811 | .821 | .797 |
| Hyland B | .956 | .966 | .953 |
| Hyland C | 1.198 | 1.312 | 1.115 |
| Serum Samples | Room Temp. | 4° C. | 37° C. |
| 1 | .661 | .633 | .689 |
| 2 | .692 | .689 | .711 |
| 3 | .616 | .654 | .680 |
| 4 | .727 | .712 | .763 |
| 5 | .665 | .700 | .687 |
| 6 | .898 | .890 | .908 |
| 7 | .866 | .884 | .887 |
| 8 | .919 | .896 | .944 |
| 9 | .854 | .863 | .881 |
| 10 | .891 | .933 | .896 |
| 11 | 1.042 | 1.051 | 1.054 |
| 12 | .990 | 1.010 | .986 |
| 13 | .969 | .990 | .986 |
| 14 | 1.023 | 1.031 | 1.033 |
| 15 | 1.160 | 1.184 | 1.138 |

| | | | |
|---|---|---|---|
| r = | .988 | r = | .990 |
| m = | 1.080 | m = | .865 |
| b = | −.055 | b = | .130 |
| Δ = | −.015 | Δ = | −.011 |
| t = | −2.190 (t.010) | t = | −1.557 (t.050) |
| DF = | 18 | DF = | 18 |
| b' = | 0 | b' = | 0 |
| m' Δ | 1.017 | m' = | 1.007 |

Table IV

Sample (B/T)/Beckman Reference Serum (B/T) as a Function of Sample Size.

| Controls | 20λ Sample | 30λ Sample |
|---|---|---|
| Beckman Control Serum | .882 | .830 |
| Hyland A | .785 | .802 |
| Hyland B | .992 | .946 |
| Hyland C | 1.214 | 1.216 |
| Serum Samples | | |
| 1 | .665 | .676 |
| 2 | .714 | .728 |
| 3 | .617 | .654 |
| 4 | .782 | .714 |
| 5 | .685 | .693 |
| 6 | .959 | .954 |
| 7 | .887 | .823 |
| 8 | .974 | .952 |
| 9 | .883 | .849 |
| 10 | .920 | .867 |
| 11 | 1.032 | 1.028 |
| 12 | 1.020 | 1.042 |
| 13 | 1.025 | .963 |
| 14 | 1.060 | 1.054 |
| 15 | 1.166 | 1.147 |

| | 30λ Sample |
|---|---|
| r = | .981 |
| m = | .951 |
| b = | .027 |
| Δ = | .017 |
| t = | 2.272 (t.010) |
| DF = | 18 |
| b' = | 0 |
| m' = | .980 |

EXAMPLE 5

A correlation of the ratios of sample B/T to Beckman reference serum B/T obtained employing separating agents made from 25 grams BSA and 150 mg BSA is given in Table V. Here again the ratios appear to not be critically dependent upon the net BSA bound to the cellulose. This data conforms the hypothesis given with respect to Table I.

Table V

Sample (B/T)/Beckman Reference Serum (B/T) as a Function of BSA Reaction Concentration.

| Controls | 25 mg BSA/gram Gel | 150 mg BSA/gram Gel |
|---|---|---|
| Beckman Control Serum | .882 | .830 |
| Hyland A | .785 | .799 |
| Hyland B | .992 | 1.000 |
| Hyland C | 1.214 | 1.273 |
| Serum Samples | | |
| 1 | .665 | .684 |
| 2 | .714 | .692 |
| 3 | .617 | .656 |
| 4 | .782 | .788 |
| 5 | .685 | .727 |
| 6 | .959 | .974 |
| 7 | .887 | .939 |
| 8 | .974 | .991 |
| 9 | .883 | .905 |
| 10 | .920 | .937 |
| 11 | 1.032 | 1.106 |
| 12 | 1.020 | 1.075 |
| 13 | 1.025 | 1.077 |
| 14 | 1.060 | 1.001 |
| 15 | 1.166 | 1.269 |

| | 150 mg BSA/gram Gel |
|---|---|
| r = | .978 |
| m = | 1.071 |
| b = | −.040 |
| Δ = | .024 |
| t = | −2.648 (t.005) |
| DF = | 18 |
| b' = | 0 |
| m' = | 1.028 |

Based upon this disclosure, many other modifications and ramifications will naturally suggest themselves to those skilled in the art of $T_3$ uptake procedures. These are intended to be comprehended as within the scope of this invention.

The embodiments of the invention in which an exclusive property or privilege is claimed are defined as follows:

1. An improved $T_3$ uptake test procedure of the type wherein:

(a) a solution is contacted with labeled $T_3$ and a separating agent;

(b) serum bound labeled $T_3$ and separating agent bound labeled $T_3$ are separated into two fractions;

(c) at least one of said fractions is measured; wherein the improvement comprises contacting said solution with a separating agent comprising bovine serum albumin covalently coupled to a derivatized polysaccharide matrix by a bifunctional coupling agent selected from a group consisting of

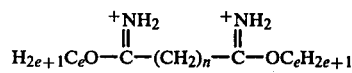

wherein n is an integer from 1 to 6 and wherein e is an integer from 1 to 2.

2. The procedure of claim 1 wherein said separating agent has a formula

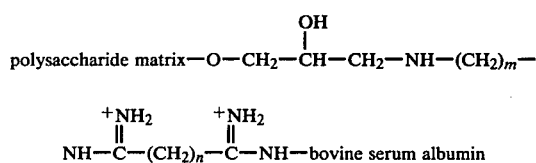

wherein m is an integer from 1 to 12.

3. The procedure of claim 2 wherein said polysaccharide matrix is selected from a group consisting of cellulosic polymers, dextran polymers, agarose, and derivatives thereof; wherein m is an integer from 4 to 6; and wherein n is an integer from 4 to 6.

4. The procedure of claim 3 wherein said label is radioactive.

5. The procedure of claim 4 wherein said label is $^{125}I$.

6. The procedure of claim 1 wherein said label is radioactive.

7. The procedure of claim 6 wherein said label is $^{125}I$.

8. The procedure of claim 1 wherein said derivatized polysaccharide matrix is a finely divided, derivatized polysaccharide matrix having an average wet maximum dimension of 1 to 18 microns.

9. The procedure of claim 8 wherein said separating agent has a formula finely divided, polysaccharide $$\text{matrix}-O-CH_2-\overset{OH}{\underset{|}{CH}}-CH_2-NH-(CH_2)_m-NH-\overset{+NH_2}{\underset{\|}{C}}-$$

$$(CH_2)_n-\overset{+NH_2}{\underset{\|}{C}}-NH-\text{bovine serum albumin}$$

wherein m is an integer from 1 to 12.

10. The procedure of claim 9 wherein said finely divided, polysaccharide matrix is selected from a group consisting of cellulosic polymers, dextran polymers, agarose, and derivatives thereof; wherein m is an integer from 4 to 6 and wherein n is an integer from 4 to 6.

11. The procedure of claim 10 wherein said finely divided polysaccharide matrix is selected from the group consisting of cellulosic polymers and derivatives thereof having an average wet maximum dimension of 10 to 15 microns.

12. The procedure of claim 11 wherein said label is radioactive.

13. The procedure of claim 12 wherein said label is $^{125}I$.

14. The procedure of claim 8 wherein said label is radioactive.

15. The procedure of claim 14 wherein said label is $^{125}I$.

16. A separating agent comprising bovine serum albumin covalently coupled to a derivatized polysaccharide matrix by a bifunctional coupling agent selected from a group consisting of $$H_{2e+1}C_eO-\overset{+NH_2}{\underset{\|}{C}}-(CH_2)_n-\overset{+NH_2}{\underset{\|}{C}}-OC_eH_{2e+1}$$

wherein n is an integer from 1 to 6 and wherein e is an integer from 1 to 2.

17. The separating agent of claim 16 having a formula $$\text{polysaccharide matrix}-O-CH_2-\overset{OH}{\underset{|}{CH}}-CH_2-NH-(CH_2)_m-$$

$$NH-\overset{+NH_2}{\underset{\|}{C}}-(CH_2)_n-\overset{+NH_2}{\underset{\|}{C}}-NH-\text{bovine serum albumin}$$

wherein m is an integer from 1 to 12.

18. The separating agent of claim 17 wherein said polysaccharide matrix is selected from a group consisting of cellulosic polymers, dextran polymers, agarose, and derivatives thereof; wherein m is an integer from 4 to 6; and wherein n is an integer from 4 to 6.

19. The separating agent of claim 16 wherein said derivatized polysaccharide matrix is a finely divided, derivatized polysaccharide matrix having an average wet maximum dimension of 1 to 18 microns.

20. The separating agent of claim 19 having a formula finely divided, polysaccharide matrix-finely divided, polysaccharide matrix—

$$O-CH_2-\overset{OH}{\underset{|}{CH}}-CH_2-NH-(CH_2)_m-NH-\overset{+NH_2}{\underset{\|}{C}}-$$

$$(CH_2)_n-\overset{+NH_2}{\underset{|}{C}}-NH-\text{bovine serum albumin}$$

wherein m is an integer from 1 to 12.

21. The separating agent of claim 20 wherein said finely divided, polysaccharide matrix is selected from a group consisting of cellulosic polymers, dextran polymers, agarose, and derivatives thereof; wherein m is an integer from 4 to 6 and wherein n is an integer from 4 to 6.

22. The separating agent of claim 21 wherein said finely divided, polysaccharide matrix is selected from the group consisting of cellulosic polymers and derivatives thereof having an average wet maximum dimension of 10 to 15 microns.

* * * * *